(12) United States Patent
Bass et al.

(10) Patent No.: US 7,105,295 B2
(45) Date of Patent: *Sep. 12, 2006

(54) METHODS FOR APPLYING SMALL VOLUMES OF REAGENTS

(75) Inventors: Jay K. Bass, Mountain View, CA (US); Jacqueline Tso, Fremont, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 555 days.

This patent is subject to a terminal disclaimer.

(21) Appl. No.: 10/229,812

(22) Filed: Aug. 27, 2002

(65) Prior Publication Data

US 2003/0008386 A1 Jan. 9, 2003

Related U.S. Application Data

(63) Continuation of application No. 09/437,990, filed on Nov. 10, 1999, now Pat. No. 6,440,669.

(51) Int. Cl.
*C12Q 1/68* (2006.01)
(52) U.S. Cl. .......................................... 435/6; 435/7.1
(58) Field of Classification Search .................. 435/6, 435/DIG. 1, DIG. 22, DIG. 34, DIG. 37, 435/DIG. 43, DIG. 44, DIG. 46, DIG. 49; 536/25.3; 436/518; 422/131, 149.11, 111
See application file for complete search history.

(56) References Cited

U.S. PATENT DOCUMENTS 4,231,047 A * 10/1980 Iwasaki et al. ............... 347/75
5,449,754 A * 9/1995 Nishioka ..................... 530/334
5,582,348 A 12/1996 Erickson et al.
5,831,070 A 11/1998 Pease et al.
5,981,733 A * 11/1999 Gamble et al. ............ 536/25.3
6,004,617 A 12/1999 Schultz et al.
6,440,669 B1 * 8/2002 Bass et al. ..................... 435/6

OTHER PUBLICATIONS

Sono Tek Corporation brochure, Milton, NY, Jul. 1996, pp. 1-5.

* cited by examiner

*Primary Examiner*—Peter Paras, Jr.
*Assistant Examiner*—Jeffrey S. Lundgren

(57) ABSTRACT

Methods, devices and apparatus are disclosed for carrying out multiple chemical reactions, such as in situ synthesis of polynucleotides, on a surface comprising an array of discrete sites. Molecules are deposited at a predetermined number of the discrete sites on the surface for reaction at the discrete sites. The surface is positioned relative to an outlet of a fluid ejection device, which is activated to dispense a small volume of a fluid through the outlet to the surface to provide uniform coating of a continuous region of the surface comprising a multiple of the discrete sites. The fluid is dispensed as uniform particles having a diameter such that the uniform particles form a sheet to coat the continuous region of the surface. In one embodiment of the present invention, liquid is dispensed as uniform particles through a fluid ejection device activated by means of ultrasonic energy. The invention has particular application to the in situ synthesis of polynucleotides in arrays on a surface.

18 Claims, 1 Drawing Sheet

METHODS FOR APPLYING SMALL VOLUMES OF REAGENTS

CROSS REFERENCE TO RELATED APPLICATIONS

This application is a continuation of U.S. patent application Ser. No. 09/437,990 (U.S. Pat. No. 6,440,669) which is a CPA filed Jun. 27, 2002 from a parent under the same Serial No. filed Nov. 10, 1999, from both of which priority is claimed under 35 U.S.C. 120 and which are incorporated herein by reference.

BACKGROUND OF THE INVENTION

1. Field of the Invention

This invention relates to the application of small volumes of reagents to surfaces. In one aspect the invention relates to the manufacture of arrays formed and arranged by depositing compounds or synthesizing large numbers of compounds on solid supports in a predetermined pattern. In another aspect this invention relates to the field of bioscience in which arrays of oligonucleotide probes are fabricated or deposited on a surface and are used to identify or analyze DNA sequences in cell matter. The present invention has a wide range of application for synthesis and use of arrays of oligonucleotides or proteins for conducting cell study, for diagnosing disease, identifying gene expression, monitoring drug response, determination of viral load, identifying genetic polymorphisms, and the like.

Significant morbidity and mortality are associated with infectious diseases and genetically inherited disorders. More rapid and accurate diagnostic methods are required for better monitoring and treatment of these conditions. Molecular methods using DNA probes, nucleic acid hybridization and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double-stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the development of methods for their incorporation into DNA and RNA has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses.

The application of nucleic acid hybridization as a diagnostic tool in clinical medicine is limited due to the cost and effort associated with the development of sufficiently sensitive and specific methods for detecting potentially low concentrations of disease-related DNA or RNA present in the complex mixture of nucleic acid sequences found in patient samples.

One method for detecting nucleic acids is to employ nucleic acid probes that have sequences complementary to sequences in the target nucleic acid. A nucleic acid probe may be, or may be capable of being, labeled with a reporter group or may be, or may be capable of becoming, bound to a support. Detection of signal depends upon the nature of the label or reporter group. Usually, the probe is comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. Commonly, binding of the probes to the target is detected by means of a label incorporated into the probe. Alternatively, the probe may be unlabeled and the target nucleic acid labeled. Binding can be detected by separating the bound probe or target from the free probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains.

Direct detection of labeled target hybridized to surface-bound probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective attachment to matching probe sites takes place. The array is then washed and imaged so as to reveal for analysis and interpretation the sites where attachment occurred.

In the preparation of arrays, reagents are applied to predetermined discrete locations on the surface of a substrate. Depending on the type of synthesis and array, the preparation may involve application of reagents at discrete locations followed by treatment of a portion or the entire surface with a different liquid reagent. The steps may be repeated a number of times sufficient to prepare the desired array. Examples of known methods for subjecting all or a portion of substrate surfaces to reagents include flooding, spin coating and flow cell assembly. Flooding the surface may be accomplished by using, for example, a multi-nozzle piezoelectric pump head. A relatively large volume of liquid is dispensed to contact the surface and assure that the dispensed reagents contact all of the desired locations. Spin coating is usually performed by dispensing the reagent at or near the center of the substrate followed by spinning to spread the reagent uniformly across the substrate.

The volume used to cover the substrate depends on the fluid property and the surface energy of the substrate. Some approaches used for in situ synthesis require a large relative volume to cover the surface because small, dispensed volumes tend to cluster and non-uniformly cover the surface. The reagent is then removed from the substrate within a high-speed spin step, which generates a considerable amount of waste. In the flow cell approach, a seal layer is brought in contact with the substrate at various support points (typically along the perimeter). A thin gap exists between the substrate and seal layer. By developing a pressure gradient across inlet and outlet channels, fluid can be forced to flow in the gap along the substrate. Although this method can use considerably less volume than the flooding method or the spin coat method, it has three major drawbacks. First, there is a long fill time in order to support laminar flow. Second, it is prone to leaking if uniform pressure is not maintained. Third, variability in surface thickness will disturb the laminar flow resulting in air pockets and hence non-uniform coverage.

2. Description of the Related Art

U.S. Pat. No. 5,831,070 (Pease, et al.) discloses printing oligonucleotide arrays using deprotection agents solely in the vapor phase.

Sono-Tek Corporation brochure, copyright 1996.

SUMMARY OF THE INVENTION

One embodiment of the present invention is a method for conducting chemical reactions on a surface comprising an array of discrete sites. Molecules are deposited at a predetermined number of the discrete sites on the surface for reaction at the discrete sites. The surface is positioned relative to an outlet of a fluid ejection device, which is activated to dispense a small volume of a fluid through the outlet to the surface to provide uniform coating of a continuous region of the surface comprising a multiple of the discrete sites. The fluid is dispensed as uniform particles having a diameter such that the uniform particles form a sheet to coat the continuous region of the surface.

Another embodiment of the present invention is a method for forming an array of molecules at discrete sites on a surface. Molecule precursors are applied to predetermined discrete sites on the surface. A small volume of a liquid is dispensed to uniformly coat a continuous region of the surface comprising a multiple of the discrete sites. The small volume of liquid is dispensed as uniform particles through a fluid ejection device activated by means of ultrasonic energy.

Another embodiment of the present invention is a method for forming an array of polynucleotides at discrete sites on a surface. Reagents are applied to predetermined discrete sites on the surface. The reagents are selected from the group consisting of nucleotides and polynucleotides. A volume of a liquid is dispensed to uniformly coat the surface with liquid. The volume of liquid is dispensed as particles of uniform diameter through a fluid ejection device activated by means of ultrasonic energy. Step (a) or step (b) may optionally be repeated.

Another embodiment of the present invention is a method for forming an array of polynucleotides at discrete sites on a surface. Nucleotide reagents are applied to predetermined discrete sites on the surface. A volume of a liquid of about 1 nanoliter to about 1000 nanoliters is dispensed to uniformly coat the surface with liquid. The liquid is dispensed as particles of uniform diameter of about 1 microns to about 500 microns through a fluid ejection device activated by means of ultrasonic energy at a frequency of about 5 kilohertz to about 300 kilohertz. The liquids comprise agents selected from the group consisting of wash liquids, deblocking agents and deprotection agents. Step (a) or step (b) optionally may be repeated.

Another embodiment of the present invention is an apparatus for forming an array of polynucleotides at discrete sites on a surface. The apparatus comprises a device for dispensing reagents to predetermined discrete sites on said surface and a fluid ejection device activated by means of ultrasonic energy. The fluid ejection device dispenses a volume of a liquid as particles of uniform diameter to uniformly coat the surface with liquid. The reagents are selected from the group consisting of nucleotides and polynucleotides.

DEFINITIONS

Figure 1:
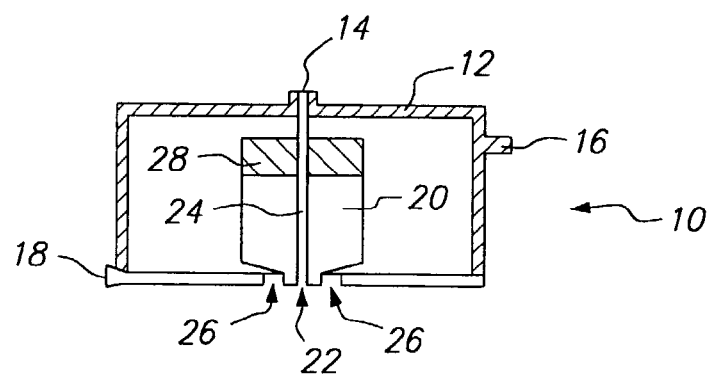
FIG. 1 is a section diagram depicting a device in accordance with the present invention.

Before proceeding further with a description of the specific embodiments of the present invention, a number of terms will be defined.

Polynucleotide—a compound or composition that is a polymeric nucleotide or, nucleic acid polymer. The polynucleotide may be a natural compound or a synthetic compound. In the context of an assay, the polynucleotide is often referred to as a polynucleotide analyte. The polynucleotide can have from about 2 to 5,000,000 or more nucleotides. The larger polynucleotides are generally found in the natural state. In an isolated state the polynucleotide can have about 2 to 50,000 or more nucleotides, usually about 10 to 20,000 nucleotides, more frequently 100 to 10,000 nucleotides. It is thus obvious that isolation of a polynucleotide from the natural state often results in fragmentation. The polynucleotides include nucleic acids, and fragments thereof, from any source in purified or unpurified form including DNA (dsDNA and ssDNA) and RNA, including tRNA, mRNA, rRNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, compounds produced synthetically, e.g., PNA as described in U.S. Pat. No. 5,948,902 and references cited therein, which can hybridize with naturally occurring nucleic acids in a sequence specific manner analogous to that of two naturally occurring nucleic acids, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

The polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, dsDNA can be heated at 90 to 100° C. for a period of about 1 to 10 minutes to produce denatured material.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides, more preferably, 15 to 30 nucleotides. The oligonucleotides include oligonucleotide probes and oligonucleotide primers.

Methods of oligonucleotide synthesis include phosphotriester and phosphodiester methods (Narang, et al. (1979) Meth. Enzymol 68:90) and synthesis on a support (Beaucage, et al. (1981) Tetrahedron Letters 22:1859–1862) as well as phosphoramidite techniques (Caruthers, M. H., et al., "Methods in Enzymology," Vol. 154, pp. 287–314 (1988)) and others described in "Synthesis and Applications of DNA and RNA," S. A. Narang, editor, Academic Press, New York, 1987, and the references contained therein.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine (A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common deoxyribonucleoside triphosphates dATP, dCTP, dGTP and dTTP and ribonucleoside triphosphates such as the four common triphosphates rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates.

Nucleotide—a base-sugar-phosphate combination that is the monomeric unit of nucleic acid polymers, i.e., DNA and RNA. The term "nucleotide" as used herein includes modified nucleotides, which a unit that contains a modified base, sugar or phosphate group.

DNA—deoxyribonucleic acid.

RNA—ribonucleic acid.

cDNA—a DNA copy of a corresponding RNA. It can be a sequence of DNA obtained by reverse transcription of an RNA molecule. It can include double-stranded or single stranded DNA obtained by amplification. An example, by way of illustration and not limitation, is the double-stranded DNA product obtained by PCR amplification of a bacterial plasmid insert. The DNA sequence inserted in the plasmid is previously obtained from reverse transcription of the corresponding RNA.

Nucleoside—is a base-sugar combination or a nucleotide lacking a phosphate moiety.

The term "support" or "substrate" refers to a porous or non-porous water insoluble material. The term "surface" refers to a surface or outer side of a support or substrate; the surface depends on the particular shape of the support or substrate. The support can have any one of a number of shapes, such as square, circular, rectangular, spherical, and the like such as found in a strip, plate, disk, and so forth. The support can be hydrophilic or hydrophobic or capable of being rendered hydrophilic or hydrophobic. Such supports include natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc., either used by themselves or in conjunction with other materials; flat glass whose surface has been chemically activated to support binding or synthesis of polynucleotides; glass available as Bioglass; other types of silicon based supports; ceramics; metals, and the like. The surface of a support may be rendered hydrophobic by treatment with a reagent such as a silane, e.g., fluoroalkylsilane, and the like. Binding of oligonucleotides to a support or surface may be accomplished by well-known techniques, commonly available in the literature. See, for example, A. C. Pease, et al., *Proc. Nat. Acad. Sci. USA*, 91:5022–5026 (1994). Other approaches are discussed briefly herein.

Monomer—a chemical entity that can be covalently linked to one or more other such entities to form an oligomer or polymer. Examples of monomers include nucleotides, modified nucleotides, amino acids, imino acids, saccharides, peptoids, and the like. In general, the monomers used in conjunction with the present invention have first and second sites (e.g., C-termini and N-termini, or 5' and 3' sites) suitable for binding of other like monomers by means of standard chemical reactions (e.g., condensation, nucleophilic displacement of a leaving group, or the like), and a diverse element that distinguishes a particular monomer from a different monomer of the same type (e.g., an amino acid side chain, a nucleotide base, etc.). The initial substrate-bound monomer is generally used as a building block in a multi-step synthesis procedure to form a complete ligand usually in a desired sequence, such as in the synthesis of oligonucleotides, oligopeptides and the like.

Oligomer—a chemical entity that contains a plurality of monomers. As used herein the terms "oligomer" and "polymer" are used interchangeably as it is generally although not necessarily smaller "polymers" that are prepared or attached using the functionalized substrates of the present invention. Example oligomers and polymers include polydeoxyribonucleotides, polyribonucleotides, other polynucleotides that are C-glycosides of a purine or pyrimidine base, or other modified polynucleotides, polypeptides, polysaccharides, and other chemical entities that contain repeating units of like chemical structure. In the practice of the present invention, oligomers generally comprise about 6 to about 20,000 monomers, preferably, about 10 to about 10,000, more preferably about 15 to about 4,000 monomers.

Amino acid—includes not only the L-, D- and non-chiral forms of naturally occurring amino acids (alanine, arginine, etc.) but also modified amino acids, amino acid analogs, and other chemical compounds that can be incorporated in conventional oligopeptide synthesis, e.g., 4-nitrophenylalanine, isoglutamic acid, isoglutamine, ε-nicotinoyllysine, isonipecotic acid, tetrahydroisoquinoleic acid, α-aminoisobutyric acid, sarcosine, citrulline, cysteic acid, t-butylglycine, t-butyl alanine, phenylglycine, cyclohexylalanine, β-alanine, 4-aminobutyric acid and the like.

Blocking and deblocking—relate to the addition and removal of chemical blocking groups using conventional materials and techniques within the skill of the art and/or described in the pertinent literature. Blocking agents are those agents that are bound to a monomer unit and which may be selectively removed therefrom to expose an active site. The blocking may be, for example, a dimethoxytrityl group and the like linked to a nucleotide by a 5'-hydroxyl position as used in polynucleotide synthesis. The blocking group may be, for example, an amine group and the like linked to an amino acid as used in the synthesis of peptides.

Protection and deprotection—relate to the addition and removal of chemical protecting groups using conventional materials and techniques within the skill of the art and/or described in the pertinent literature; for example, reference can be made to Greene, et al., Protective Groups in Organic Synthesis, $2^{nd}$ Ed., New York, John Wiley & Sons (1991). Protecting groups prevent the site to which they are attached from participating in the chemical reaction to be carried out. Usually, the protecting groups may be selectively removed to expose an active site.

DETAILED DESCRIPTION OF THE INVENTION

In its broadest application the present invention is directed to methods for conducting chemical reactions on a surface of a substrate at discrete sites comprising an array. The chemical reactions may be concerned, for example, with the synthesis of molecules on the surface of the array or with carrying out a diagnostic procedure utilizing the array. In carrying out such chemical reactions one or more steps may involve delivering a volume of fluid to a surface to provide uniform coating of a continuous region of the surface comprising a multiple of the discrete sites. In these steps a fluid ejection device is employed that is activated to dispense a small volume of fluid through an outlet to the surface. The present invention is applicable to situations in which liquids have previously been dispensed by known methods to a surface by flooding the surface or a portion thereof with liquid. In the present invention fluid is dispensed as uniform particles having a diameter such that the uniform particles form a thin sheet to coat the desired region of the surface.

A number of advantages over the known methods may be realized in the practice of the present invention. The present method produces a thinner layer of liquid deposited on a surface than that produced by prior methods such as flow cell assembly. Such an advantage is particularly important for surfaces that are hydrophobic because it avoids the beading and non-uniform coverage that results when larger quantities of liquid are applied to the surface. Uniform coverage of a hydrophobic surface is achievable with the present invention because the small volume of liquid dispensed tends to form a layer on the surface rather than form beads. Liquid movement to hydrophilic sites on the surface is promoted. Another advantage of the present invention is that liquid accumulates at the discrete sites on the surface in a more facile manner than in methods known in the art. This surprising result further facilitates bringing reagents to the desired locations for reaction at the discrete sites. Such an advantage is particularly important in the present invention in which very small volumes of liquid are dispensed to the surface. A further advantage of the present invention is that multiple thin layers of liquid may be applied to the surface in a particular step. As a result diffusion of reagents is greatly reduced. This is important because fresh reagents may be supplied to the sites of reaction by applying successive 2 to 5 separate thin layers of reagents over a short period of time in accordance with the present invention. In known methods such as flow cell assembly techniques the layers of liquid are much thicker. After reaction of reagents at the site, additional reactants from the liquid must diffuse to the reaction site.

The present invention has application generally to conducting chemical reactions on a surface of a support or a substrate. The present invention is described herein for purposes of illustration primarily with regard to the synthesis of arrays of oligonucleotides. However, the invention has application to the preparation of other molecules as well as to other types of manipulations involving chemical reactions. The types of chemical reactions that may be carried out using the present invention include, by way of illustration and not limitation, synthesis of polymeric materials such as biomolecules, e.g., polynucleotides including oligonucleotides and proteins including peptides, polyalcohols such as polysaccharides, e.g., carbohydrates, oligosaccharides, and the like; conjugation of molecules such as the conjugation of reporter groups or labels to nucleic acids or nucleotides, proteins such as enzymes, antibodies, and the like; diagnostic procedures such as assays involving ligands and receptors such as antibody-antigen or antibody-hapten binding, nucleic acid hybridization, and so forth; molecular biological reactions such as those involving enzymes, e.g., amplification procedures such as polymerase chain reaction, ligase chain reaction, restriction enzyme reactions; and so forth. The present invention has particular application to chemical reactions involving multiple steps and a large number of compounds such as in the synthesis of combinatorial libraries and polynucleotide and peptide arrays.

The methods and reagents of the present invention are particularly useful in the area of the preparation of oligonucleotide arrays and, in particular, the preparation of such arrays by in situ synthesis. In the field of bioscience, arrays of oligonucleotide probes, fabricated or deposited on a surface, are used to identify DNA sequences in cell matter. The arrays generally involve a surface containing a mosaic of different oligonucleotides or sample nucleic acid sequences that are individually localized to discrete, known areas of the surface. In one approach, multiple identical arrays across a complete front surface of a single substrate are used. However, the arrays produced on a given substrate need not be identical and some or all could be different. Each array may contain multiple spots or features and each array may be separated by spaces. A typical array may contain from 100 to 100,000 or more features. Each oligonucleotide on the array has a length typically in the range of about 10 to about 100 base pairs. All of the features may be different, or some or all may be the same. Each feature may carry a predetermined polynucleotide having a particular sequence or a predetermined mixture of polynucleotides. While arrays may be separated from one another by spaces, and the features may be separated from one another by spaces, such spaces in either instance are not essential.

The size of the array may be varied depending on the application as discussed herein. Fewer or more discrete sites may be employed, depending on the nature of the chemical reactions involved, cost considerations, and so forth. The spacing between sites on the device is determined by the ease of fabrication, the requirement for resolution between the various sites, and the number of sites desired on a device. However, particular spacing between sites or special arrangement or geometry of the sites is not necessary for device function. Any combination of micro-locations can operate over the complete area of the surface. As mentioned above, molecules such as specific binding molecules, chemical and analytical reagents, and the like may be attached to the surface.

Ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

Various ways may be employed to produce an array of polynucleotides on supports or surfaces such as glass, metal, plastic and the like. Such methods are known in the art. One such method is discussed in U.S. Pat. No. 5,744,305 (Fodor, et al.) and involves solid phase chemistry, photolabile protecting groups and photolithography. Binary masking techniques are employed in one embodiment of the above. In another approach ink jet technology may be used to spot polynucleotides and other reagents on a surface as described, for example, in PCT application WO 89/10977. Other methods include those disclosed by Gamble, et al., WO97/44134; Gamble, et al., WO98/10858; Baldeschwieler, et al., WO95/25116; Brown, et al., U.S. Pat. No. 5,807,522; and the like.

In the above approaches to forming arrays using in situ synthesis, the chemistry involved may include monomers that are nucleoside triphosphates used to form the polynucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling. One preferred coupling method is the phosphoramidite coupling, which is a phosphite coupling. In using this coupling method, after the phosphite coupling is complete, the resulting phosphite is oxidized to a phosphate. Oxidation can be effected with oxygen to give phosphates or with sulfur to give phosphorothioates. The phosphoramidites are dissolved in anhydrous acetonitrile to give a solution having a given ratio of amidite concentrations. The mixture of known chemically compatible monomers is reacted to a solid support, or further along, may be reacted to a growing chain of monomer units. For a more detailed discussion of the chemistry involved in the above synthetic approaches, see, for example, U.S. Pat. No. 5,436,327 at column 2, line 34, to column 4, line 36, which is incorporated herein by reference in its entirety.

As seen from the above discussion, arrays may be fabricated in situ, adding one base pair at a time to a primer site. Affymetrix, for example, uses photolithography to uncover sites, which are then exposed and reacted with one of the four base pair phosphoramidites. In photolithography the surface is first coated with a light-sensitive resist, exposed through a mask and the pattern is revealed by dissolving away the exposed or the unexposed resist and, subsequently, a surface layer. A separate mask must be made for each pattern, which may involve four patterns for each base pair in the length of the probe. Much overhead is involved in preparing the masks for photolithography, which may number 80 for probes of length 20, thus rendering this technique best suited for very high volume production. There are also problems in controlling the etching reaction and in registering masks between each step.

Another in situ method employs inkjet printing technology to dispense the appropriate phosphoramidite onto the individual probe sites. For example, see U.S. Pat. No. 5,700,637 and PCT WO 95/25116. Another method involves electrochemically patterning a surface. An electrolyte overlying the surface and an array of electrodes adjacent to the surface and in contact with the electrolyte is provided. The potential of one or more electrodes of the array is altered so as to deposit or remove or chemically modify a substance on the surface adjacent the electrode. Several such treatments may be performed in sequence using different electrodes of the array. The method may be used for step-wise chemical synthesis of, for example, oligonucleotides tethered to the surface.

In a similar approach a self-addressable, self-assembling microelectronic device is used to carry out and control multi-step and multiplex molecular biological reactions, such as biopolymer synthesis, nucleic acid hybridization, antibody-antigen reaction, and diagnostics, in microscopic formats. The device electronically can control the transport and attachment of specific binding entities and other reactants to specific micro-locations.

Array plates have been disclosed where a glass support surface is coated with a positive or negative photoresist substance and then exposed to light and developed to create a patterned region of a first exposed surface and a photoresist coated surface on the support. The first exposed surface is reacted with a fluoroalkylsilane to form a stable fluoroalkylsiloxane hydrophobic matrix on the first exposed surface. The photoresist coat on the surface is removed so as to form a second exposed surface, which is reacted with a hydroxy- or aminoalkylsilane so as to convert the second exposed surface to a derivatized hydrophilic binding site region and thus form the array plate.

Many other methods have been put forth for fabricating such arrays. In one approach oligonucleotide probes are spotted on a suitable surface to produce an array. For this purpose, pre-synthesized probes are employed. In another approach a substrate is prepared upon which is located microdrop-sized loci at which chemical compounds are synthesized or diagnostic tests are conducted. The loci are formed by applying microdrops from which a microdrop is pulse-fed onto the surface of the substrate.

In other disclosures U.S. Pat. No. 5,474,796 (Brennan) discloses a method for making array plates. U.S. Pat. No. 5,445,934 (Fodor, et al.) discusses an array of oligonucleotides on a solid substrate.

The present invention has application to the aforementioned methods for fabricating arrays. In one aspect the invention concerns a method for forming an array of molecules at discrete sites on a surface. Molecule precursors are applied to the surface at discrete sites. The molecule precursors may be monomers such as, for example, amino acids, nucleotides, saccharides, peptoids, and the like, or polymers including polysaccharides, polymers having drugs linked to a polymeric backbone, biopolymers such as poly (amino acids) such as peptides and proteins, oligonucleotides, polynucleotides, and the like. Accordingly, the invention herein has application to both in situ synthesis as well as the synthesis of molecules by attachment of whole molecules to a surface. In either of the above synthetic approaches, the methods may include one or more steps involving contacting the surface comprising the discrete sites with solutions of monomers or polymers which may also contain activators such as tetrazole, DCI and the like; solutions of coupling reagents such as, e.g., phosphoramidites such as cyanoethyl phosphoramidite nucleotides; solutions of capping reagents to truncate unreacted nucleosides from further participation in subsequent monomer addition cycles such as, e.g., acetic anhydride and 1-methylimidazole to acetylate free 5'-hydroxyl groups; wash solutions such as organic solvents or buffers to remove unreacted reagents; solutions of chemical reactants such as blocking and deblocking agents such as protic solvents, trichloroacetic acid, dichloroacetic acid and the like; protecting and deprotecting reagents; acidic solutions such as, e.g., solutions of acids for removal of dimethoxytrityl groups by acid hydrolysis; basic solutions; solutions of oxidizing agents such as, e.g., iodine in tetrahydrofuran/water/pyridine and the like; solutions of reducing agents; solutions of carrier materials; and so forth. The present invention may be employed to dispense liquids in all of the above circumstances.

The attachment chemistry for carrying out the known synthetic methods is sometimes referred to a "priming" the surface. To this end, the surface is modified so as to prepare the surface for attachment of the monomeric building blocks. This surface may be the surface itself or an overcoat layer. The surface may be modified with groups or coupling agents to covalently link the initial nucleoside to the surface. Representative groups include, by way of illustration and not limitation, amino, especially primary amino, hydroxyl, thiol, sulfonic acid, phosphorous and phosphoric acid, particularly in the form of acid halides, especially chloride and bromide, and carboxyl, and the like. The reactive groups are conveniently attached to the surface commonly through a hydrocarbyl radical such as an alkylene or phenylene divalent radical.

In one embodiment, the present invention has application to the deblocking steps often utilized in oligonucleotide synthesis wherein there may be several sites on a nucleoside, for example, of similar chemical nature, e.g., hydroxyl groups. The synthesis may involve blocking certain sites from reaction with protecting groups. Nucleoside reagents may be used that comprise the blocking group. As explained above, a blocking group is one that is chemically bound to a monomer unit and which may be removed. The blocking group is attached temporarily to a potentially reactive site so as to prevent it from reacting. The blocking group assists in avoiding unwanted side reactions. The blocking groups are generally stable during the reactions involved and yet removable to yield the original site. The present invention may also be used in the latter stages of the synthesis to dispense deprotecting agents for removal of protecting groups.

Phosphoramidite chemistry and solid phase oligonucleotide synthesis protocols often use a blocking group such as a dimethoxytrityl protecting group for the 5'-hydroxyl of nucleosides. A phosphoramidite functionality is utilized at the 3'-hydroxyl position. Phosphoramidite synthesis generally proceeds form the 3' to the 5' of the ribose or deoxyribose sugar component of he phosphoramidite nucleoside. The 5' end of the growing chain is coupled with the 3' phosphoramidite of the incoming base to form a phosphite triester intermediate. The 5'-hydroxyl of the added base is often blocked by a blocking group so only one new base is added to the growing chain at a time. Any unreacted 5'-hydroxyl groups are capped off to stop the synthesis of this chain, which would be one base short at the end of the synthesis. The triester intermediate is subjected to iodine oxidation after each coupling reaction to yield a more stable phosphotriester intermediate. Without oxidation, the unstable phosphite triester linkage cleaves under the acidic conditions of subsequent synthesis steps.

Attachment and removal of the blocking groups generally is effected globally by one of the methods mentioned above such as flooding the surface, spin coating and flow cell assembly. In accordance with one aspect of the present invention, a continuous region of the surface comprising a multiple of discrete sites is exposed to a solution comprising reagents for conducting the deblocking step.

By the term "discrete sites" is meant a specific region, e.g., spot, point or the like, on a surface that contains a feature such as a molecule precursor, molecule, and so forth. The discrete sites may be isolated or non-isolated, shielded or unshielded, continuous or discontinuous, connected or unconnected. The discrete sites may be established by etching, barrier formation, masking, and the like or by depositing reagents on a surface. By the term "continuous region comprising a multiple of discrete sites" is meant a portion of, or the entire surface, comprising the active discrete sites as distinguished from the discrete sites themselves. Usually, the solution comprising such reagents is contacted with the entire surface comprising the discrete sites.

Usually, the present methods involve positioning the surface relative to the outlet of a fluid ejection device. For example, the surface may be mounted on a linear stage and moved in position relative to the fluid ejection device above the stage. In another approach the surface may be rotated to the fluid ejection device, which is moved radially relative to the surface. Other ways of positioning the surface relative to the fluid ejection device include a combination of the above approaches.

The nature of the fluid ejection device is dependent on the type of energy used to activate the device. In general, the fluid ejection device should be capable of dispensing a small volume of fluid through an outlet to provide uniform coating of the continuous region of the surface. To provide such uniform coating the fluid should be dispensed as particles of substantially uniform size. The term "substantially uniform size" means that the diameter of each of the particles does not vary more than about 50%, usually, not more than about 25% and desirably not more than about 5 to about 0%. The variation in the diameter of the particles can be tolerated to a greater degree where the particles are within the average diameter range set forth below. The average diameter of the particles is generally about 1 to about 200 microns, usually, about 10 to about 150 microns, more usually, about 15 to about 100 microns. Preferably, the particles of fluid are dispensed as a mist. The diameter of the outlet should be larger than the diameter of the particles to avoid clogging of the outlet. The diameter of the outlet, therefore, should be about 10 to about 250 times as large, usually about 40 to about 150 times as large, as the average diameter of the particles. In general, the diameter of the outlet is about 50 microns to about 250 millimeters, usually, about 150 to about 25 millimeters.

One consideration for the dimensions of the nozzle relates to the shape of the spray desired. The spray may be conical, flat, narrow such as in a microspray, and the like. For conical spray the diameter of the outlet usually falls in the upper part of the ranges set forth above for the diameter of the outlet in general. For flat spray the diameter of the outlet usually falls in the middle of the above range and for microspray the diameter of the outlet usually falls in the lower part of the above range. Another consideration in the dimensions of the outlet and in the energy levels used for dispensing the liquid is the viscosity of the liquid. In general, the higher the viscosity of the liquid, the greater the energy levels and the greater the dimensions of the outlet. The viscosity of the liquid should allow the liquid to be dispensed as uniform particles as discussed above. Accordingly, the viscosity of the liquid is generally about 0.1 to about 10 centipoise, usually about 0.5 to about 2.5 centipoise. The fluid ejection device is usually a nozzle that comprises a nozzle stem having an outlet. Other types of outlets and configurations may be employed. Compressed air may be employed to assist in focusing the liquid exiting the outlet. Usually, the compresses air is dispensed through a channel adjacent the outlet. The pressure employed may be about 0.1 to about 5 pounds per square inch.

The volume of liquid dispensed is usually about 1 to about 1000 nanoliters per square centimeter of surface, more usually, about 20 to about 100 nanoliters per square centimeter. In general, the volume of liquid is a minimal volume to provide uniform coating of the surface. The layer of coating of liquid provided in the present invention is about 5 to about 1000 microns, usually about 20 to about 500 microns, more usually, about 25 to about 125 microns. The primary concern in coating the surface uniformly is that the necessary amount of reagents is delivered to the discrete sites within the continuous region that is exposed to the liquid. One wishes to deliver reagents such as deprotection reagents to all of the desired sites so that the reagent may accomplish its expected purpose. The prior art approaches accomplish such delivery by exposing the surface to a considerable excess volume of the liquid containing the reagents. We have found unexpectedly and against the wisdom in the art that coating the surface uniformly with liquid reagents using a minimal amount of liquid dispensed in particulate form as described above successfully accomplishes the above purpose.

The liquid is dispensed in about 0.1 to about 10 seconds, usually about 0.5 to about 5 seconds. It is an advantage of the present invention that a short dispense time may be utilized compared to some of the techniques of the prior art. The flow rate for liquid into the nozzle of a suitable device should be about 10 microliters to about 5000 microliters per second, usually about 200 to about 3000 microliters per second. In general, the range for flow rate is large for ultrasonic activation since atomization relies only on liquid being introduced onto the atomizing surface and not on pressure.

The nozzle of a fluid ejection device may be fabricated from any material that is compatible, usually substantially non-reactive, with the liquid and reagents to be dispensed and with the particular means of activation employed for the device. The materials include, by way of example and not limitation, metal such as stainless steel, titanium, platinum, etc., plastic, ceramic, Teflon®-coated materials and the like. Various parts of the nozzle may be fabricated from different materials depending on the function of the part.

The fluid ejection device may be activated by means of ultrasonic energy, mechanical energy, electrical energy, thermal energy and the like. Examples of fluid ejection devices that are activated by mechanical, thermal or electrical energy include, e.g., inkjet devices and the like.

Preferably, the fluid ejection device is activated by ultrasonic energy. An ultrasonic dispense head such as a nozzle may be used to produce a fine mist of liquid reagent over a substrate. By moving the nozzle relative to the substrate, the surface can be coated with a minimal volume of liquid (thin mist layer). The coating process is fast and free of mechanical obstructions. High frequency sound waves are employed using ultrasonic nozzles to produce atomization. The ultrasonic energy typically has a frequency of about 5 to about 300 kHz, usually, about 25 to about 150 kHz. For ultrasonic atomization power levels are generally from about 0.1 to about 50 watts, usually about 1 to about 15 watts. It should be noted that the power levels are generally chosen to maximize efficiency. Any ultrasonic device that is capable of producing a spray of liquid having the characteristics discussed above may be employed in the present method.

FIG. 1 depicts a fluid ejection device in accordance with the present invention. The device 10 comprises housing 12 having fluid inlet 14, which typically is in fluid communication with a reservoir (not shown). Housing 12 also has an input orifice 16 that is in communication with an ultrasonic generator (also not shown). Air inlet 18, which is in communication with a source of compressed air (also not shown), is also present in housing 12. Fluid inlet 14 communicates with nozzle body 20 at one end thereof. At the other end of 20 is droplet outlet 22, which is in communication with inlet 14 by means of channel 24. Housing 12 also has air outlet 26 adjacent droplet outlet 22. Nozzle body 20 comprises piezo transducers 28, which are coupled to body 20.

A particular device for accomplishing the purposes of the present invention is one in which high frequency electrical energy from an ultrasonic generator is received by a transducer such as a piezoelectric transducer, which converts such energy into vibratory mechanical motion at the same frequency. Amplifiers may be coupled to the transducers to amplify the motion. In one approach amplification may be realized by a step transition from a large to a small diameter of a front horn of the nozzle. The excitation created by the transducers produces standing waves along the length of the nozzle. The amplitude of the wave is maximized at the atomizing surface, which is usually located at the end of a small diameter portion of the nozzle. Compressed air at a pressure of about 0.5 to about 1.5 psi, typically about 1 psi is introduced into an ultrasonic device, usually into a diffusion chamber of an air shroud of such a device. A uniformly distributed flow of air is produced around the nozzle stem of the device. An ultrasonically produced spray at the tip of the nozzle stem is immediately entrained in the air stream. An adjustable focusing mechanism on the air shroud allows complete control of the width of the spray. The spray envelope is bow-shaped. The width of the bow is controlled by moving the focus adjust mechanism in and out. The distance between nozzle and substrate can be varied from near contact to approximately two inches. Liquid may be introduced onto an atomizing surface through a large, non-clogging feed channel running the length of the nozzle. Liquid absorbs the vibrational energy resulting in the atomization of the liquid. One such ultrasonic fluid ejection device is that manufactured by Sono-Tek Corporation, Milton N.Y., and sold under the trademark ACCUMIST ultrasonic fluid ejection device.

The fluid that is delivered in accordance with the present invention is usually a liquid, the nature of which depends on the nature of the reagents to be dispensed to the surface. The liquid may be a protic solvent or an aprotic solvent. Usually, it is desirable to conduct reactions in a protic solvent because of the nature of the reagents and surfaces involved. The liquid may be an aqueous medium that is solely water or solely an organic solvent. An aqueous medium may contain from about 0.01 to about 97 or more volume percent of a cosolvent such as an organic solvent. Organic solvents include by way of illustration and not limitation oxygenated organic solvents of from 1–6, more usually from 1–4, carbon atoms, including alcohols such as methanol, ethanol, propanol, etc., ethers such as tetrahydrofuran, ethyl ether, propyl ether, etc., dimethylformamide, dimethylsulfoxide, 1,4-dioxane, N-methyl-2-pyrrolidone (NMP), acetonitrile and the like. Usually these cosolvents, if used, are present in less than about 70 weight percent, more usually in less than about 30 weight percent.

The pH for the liquid depends on the nature of the reagents, i.e., deprotection, protection, wash solution and the like and is generally selected to achieve optimum reaction between the molecules and reagents or to effectively wash a surface. The pH range is broad because some of the reagents dispensed include acids and bases. The pH is usually in the range of about 1 to about 14. Among the factors that must be considered are the pH dependence of the reactive molecules, the stability of the molecules at different pH values, and so forth. Various buffers may be used to achieve the desired pH and maintain the pH during the reaction. Illustrative buffers include acetate, borate, phosphate, carbonate, and the like. The particular buffer employed is not critical to this invention as long as the buffer does not react unintentionally with the reagents or the synthesized molecules. Further, in an individual reaction or a wash step, one or another buffer may be preferred.

The fluid ejection device is in fluid communication with a reservoir containing the liquid to be dispensed. It is within the purview of the present invention that the fluid ejection device is in alternating fluid communication with a plurality of reservoirs each containing a different liquid. The liquids may differ by the presence of different reagents and the like. The number of steps for dispensing liquids in accordance with the present invention depends on the nature of the chemical reaction such as synthesis or diagnostic procedure, being conducted, e.g., in situ synthesis, synthesis by direct attachment, assay for an analyte, etc. The number of separate distinct steps for dispensing liquids may be as few as one or a great as five for any particular reagent dispensed. Furthermore, for any one of the separate distinct steps liquid may be applied by dispensing such liquid one or more times. As mentioned above, one of the advantages that may be realized with the present invention is that the liquid may be applied in thin layers and several applications of thin layers of liquid may be employed for each reaction or wash and the like.

In one embodiment of the present invention phosphoramidite reagents are deposited in an array pattern on a substrate by means of inkjet technology. The substrate surface is then coated with an oxidation reagent by applying the liquid oxidation reagent to the surface using a dispense head activated by ultrasonic energy. The surface of the substrate is then washed with a wash solution such as an organic solvent, e.g., acetonitrile, to remove excess and unreacted reagents. The wash liquid may be applied using a dispense head activated by ultrasonic energy. The surface is coated uniformly with a deblocking reagent applied again using a dispense head activated by ultrasonic energy. The surface is washed as described above and phosphoramidite reagents are applied in a pattern using inkjet technology as discussed above. The steps described above are repeated for a sufficient number of times to create the desired length of oligonucleotides on the array.

The oligonucleotide arrays constructed in accordance with the present invention may be used to carry out nucleic acid hybridization in a diagnostic fashion. To this end the array is exposed to a solution containing the polynucleotide analytes in the usual manner and labeled DNA fragments selectively hybridize at sites where a complementary oligonucleotide is found. The present method may be employed to dispense the solution containing the polynucleotide analytes, a wash solution, and so forth.

Figure 2:
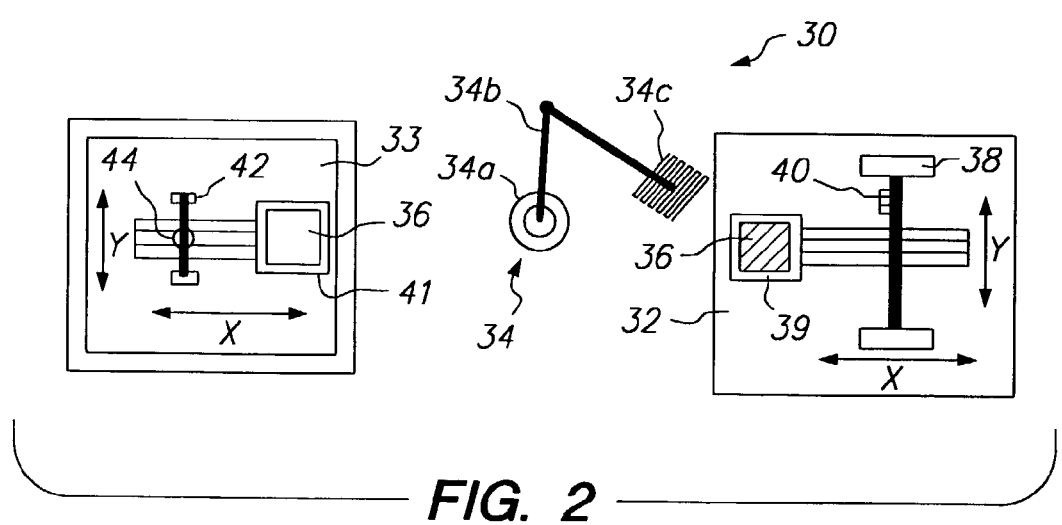
FIG. 2 is a schematic diagram depicting an apparatus in accordance with the present invention.

As mentioned above, one embodiment of the present invention, by way of illustration and not limitation, is an apparatus for forming an array of polynucleotides at discrete sites on a surface. The apparatus comprises a device for dispensing reagents to predetermined discrete sites on said surface and a fluid ejection device activated by means of ultrasonic energy. The fluid ejection device dispenses a volume of a liquid as particles of uniform diameter to uniformly coat the surface with liquid. The reagents are selected from the group consisting of nucleotides and polynucleotides. Referring to FIG. 2, apparatus 30 is shown that comprises first platform 32 and second platform 33, each mounted on a main platform (not shown) of apparatus 30. Transfer robot 34 is also mounted on the main platform of apparatus 30 and comprises base 34a, arm 34b that is movably mounted on base 34a, and wafer transporter 34c that is attached to arm 34b. Substrate wafer 36 is removably resting on first linear stage 39, which is movably mounted on first platform 32 and moveable in the x direction. Second linear stage 38 is affixed to first platform 32. Inkjet piezo module 40 is mounted on second linear stage 38 and is movable in the y direction. Second platform 33 comprises third linear stage 41, which is mounted on second platform 33 and is moveable in the x-direction. Fourth linear stage 42 is affixed to second platform 33 and ultrasonic fluid ejection device 44 is mounted on fourth linear stage 42. Device 44 may be affixed centrally on fourth linear stage 42 or it may be mounted on fourth linear stage 42 to be moveable in the y-direction.

In use, substrate wafer 36, on which an array of polynucleotides is to be formed, is removably secured on first linear stage 39. Inkjet piezo module 40 is activated to deposit phosphoramidite reagents on the surface of wafer 36 at discrete sites. First linear stage 39 is moved along the x-axis and inkjet piezo module 40 is moved along the y-axis. Subsequently, transfer robot 34 is activated to move arm 34b so that wafer transporter 34c removes substrate wafer 36 from first linear stage 39. Arm 34b of transfer robot 34 is moved so that wafer transporter 34c delivers substrate wafer 36 to third linear stage 41. Ultrasonic fluid ejection device 44 is activated to dispense a liquid reagent that comprises an oxidizing reagent to uniformly coat the surface of wafer 36 with a thin layer of the liquid reagent. In that regard third linear stage 41 is moved along the x-axis; and, if device 44 is moveably mounted on fourth linear stage 42, device 44 is moved along the y-axis.

Additional steps in the synthesis of an array of polynucleotides on the surface of wafer 36 are carried out as described above using apparatus 30. For example, while substrate wafer 36 remains at second platform 33, ultrasonic fluid ejection device 44 is activated to dispense a wash liquid. Prior to contact with a wash liquid, wafer 36 may be treated to remove excess and unreacted reagents. Such treatment may be by spinning, suction or vacuum, contact with an inert gas and so forth. For example, an air jet may be mounted on fourth linear stage 42 and may be used to dispense a stream of an inert gas such as nitrogen, argon and the like to dry the surface of wafer 36.

For dispensing wash liquid and other liquids, device 44 is in fluid communication with more than one reservoir (reservoirs not shown) containing the appropriate liquid reagents or wash liquids for use in the above steps or in subsequent steps. Suitable valving mechanisms are employed to permit establishment and disengagement of various desired fluid communications.

Following the washing step and while substrate wafer 36 remains at second platform 33, ultrasonic fluid ejection device 44 is activated to dispense a deblocking reagent to uniformly coat the surface of substrate wafer 36. Again, excess liquid and reagents may be removed from the surface of wafer 36 and, while substrate wafer 36 remains at second platform 33, ultrasonic fluid ejection device 44 is activated to dispense a wash liquid to wash the surface of wafer 36. Subsequently, transfer robot 34 is activated to move arm 34b so that wafer transporter 34c removes substrate wafer 36 from third linear stage 41. Arm 34b of transfer robot 34 is moved so that wafer transporter 34c delivers substrate wafer 36 to first linear stage 39. Inkjet piezo module 40 is activated to deposit phosphoramidite reagents on the surface of wafer 36 at discrete sites. It should be understood that the above steps may be repeated a sufficient number of times so that the desired polynucleotides are synthesized in an array on the surface of substrate wafer 36. It should also be understood that each step may include one or more dispensing actions in accordance with the present invention as explained hereinabove.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for forming an array of nucleotide polymers at discrete sites on a surface, said method comprising:
    (a) applying nucleotide polymer precursor reagents to predetermined discrete sites on said surface, said discrete sites being activated for attachment of the reagents thereto,
    (b) dispensing a volume of a liquid to uniformly coat the entire surface comprising said discrete sites with liquid, said volume of liquid being dispensed as particles of uniform diameter through a fluid ejection device activated by means of ultrasonic energy to provide a layer of liquid on said surface, said layer having a thickness of 20 to 500 microns, and
    (c) repeating step (a) and/or step (b) to form said array of nucleotide polymers, wherein step (a) is repeated at least once when said reagents are nucleotides.

2. The method according to claim 1 wherein said liquid comprises an agent selected from the group consisting of washing solutions, buffers, deblocking agents, blocking agents, oxidizing agents, reducing agents and phosphoramidite reagents.

3. The method according to claim 1 wherein said surface is essentially planar.

4. The method according to claim 1 wherein said liquid is dispensed from an outlet of said fluid ejection device as a mist.

5. The method according to claim 1 wherein step (a) is carried out by an application technology selected from the group consisting of printing technology, masking technology, ultrasonic technology and combinations thereof.

6. The method according to claim 1 wherein said particles of uniform diameter have a diameter on the average of about 10 microns to about 150 microns.

7. The method according to claim 1 wherein said ultrasonic energy has a frequency of about 5 kilohertz to about 300 kilohertz.

8. The method according to claim 1 wherein said volume of liquid is about 1 nanoliter to about 1000 nanoliters per square centimeter.

9. The method according to claim 1 wherein said surface is mounted on a linear stage and moved in position relative to said fluid ejection device above said stage.

10. The method according to claim 1 wherein said surface is rotated relative to said fluid ejection device and said fluid ejection device is moved radially relative to said surface.

11. The method according to claim 1 wherein said fluid ejection device is in fluid communication with a reservoir containing said liquid.

12. The method according to claim 1 wherein said fluid ejection device is in alternating fluid communication with a plurality of reservoirs each containing a different liquid.

13. A method for forming an array of polynucleotides at discrete sites on a surface, said method comprising:
    (a) applying polynucleotide precursor reagents to predetermined discrete sites on said surface, said discrete sites being activated for attachment of the reagents thereto,
    (b) dispensing a volume of a liquid of about 1 nanoliter to about 1000 nanoliters per square centimeter to uniformly coat the entire surface comprising said discrete sites with liquid to provide a layer of liquid on said surface, said layer having a thickness of 20 to 500 microns, said volume of liquid being dispensed as particles of uniform diameter of about 10 microns to about 150 microns, wherein the diameter of each of the particles does not vary more than about 50%, through a fluid ejection device activated by means of ultrasonic energy at a frequency of about 5 kilohertz to about 300 kilohertz, and
    (c) repeating step (a) wherein step (b) is optionally repeated prior to or after repeating step (a) and wherein step (a) and/or step (b) is repeated until said array of polynucleotides is formed.

14. The method according to claim 13 wherein said liquids comprise agents selected from the group consisting of washing solutions, buffers, oxidizing agents, reducing agents, deblocking agents and blocking agents.

15. The method according to claim 13 wherein step (b) is repeated at least one time prior to repeating step (a) to dispense multiple layers of said liquid on said surface.

16. The method according to claim 15 wherein said liquid is dispensed as a layer of about 25 to 125 microns in thickness.

17. A method for forming an array of nucleotide polymers at discrete sites on a surface, said method comprising:
    (a) applying nucleotide polymer precursor reagents to predetermined discrete sites on said surface, said discrete sites being activated for attachment of the reagents thereto,
    (b) dispensing a volume of a liquid to uniformly coat the entire surface comprising said discrete sites with liquid, said volume of liquid being dispensed as particles of uniform diameter through a fluid ejection device activated by means of ultrasonic energy to provide a layer of liquid on said surface, and
    (c) repeating step (a) and/or step (b) to form said array of nucleotide polymers, wherein step (a) is repeated at least once when said reagents are nucleotides.

18. The method according to claim 17 wherein said liquid comprises an agent selected from the group consisting of washing solutions, buffers, deblocking agents, blocking agents, oxidizing agents, reducing agents and phosphoramidite reagents.

* * * * *